(12) United States Patent
Bondar et al.

(10) Patent No.: US 8,268,238 B2
(45) Date of Patent: Sep. 18, 2012

(54) SYSTEM AND METHOD FOR RECYCLING STERILANT GAS

(75) Inventors: Douglas E. Bondar, Martinez, GA (US); Michael L. Bongiovi, Evans, GA (US)

(73) Assignee: Tyco Healthcare Group LP, Mansfield, MA (US)

( * ) Notice: Subject to any disclaimer, the term of this patent is extended or adjusted under 35 U.S.C. 154(b) by 87 days.

(21) Appl. No.: 12/861,040

(22) Filed: Aug. 23, 2010

(65) Prior Publication Data

US 2010/0313962 A1    Dec. 16, 2010

Related U.S. Application Data

(60) Continuation-in-part of application No. 12/637,064, filed on Dec. 14, 2009, which is a division of application No. 11/541,358, filed on Sep. 29, 2006, now Pat. No. 7,666,369.

(51) Int. Cl.
*A61L 2/20* (2006.01)
(52) U.S. Cl. ............ 422/3; 422/28; 422/31; 422/105; 422/110; 422/292; 422/295; 436/1; 436/55
(58) Field of Classification Search ............... 422/3, 28, 422/31, 105, 110, 292, 295; 436/1, 55
See application file for complete search history.

(56) References Cited

U.S. PATENT DOCUMENTS

| | | | |
|---|---|---|---|
| 251,925 A | 1/1882 | Nietscke |
| 867,831 A | 10/1907 | Nathan |
| 1,126,430 A | 1/1915 | Elliott |
| 1,675,123 A | 6/1928 | Metzger at al. |
| 1,900,717 A | 3/1933 | Kilbourne |
| 2,131,134 A | 9/1938 | Baer et al. |
| 2,253,287 A | 8/1941 | Davis et al. |
| 2,465,853 A | 3/1949 | Dalton, Jr. |
| 3,097,916 A | 7/1963 | Dawson et al. |
| 3,238,096 A | 3/1966 | Kaye |
| 3,341,280 A | 9/1967 | Eolkin |
| 3,372,980 A | 3/1968 | Satas |
| 3,495,932 A | 2/1970 | Tuma |
| 3,549,312 A | 12/1970 | Ernst |
| 3,600,127 A | 8/1971 | Kereluk at al. |
| 3,758,257 A | 9/1973 | Dastur |
| 3,767,362 A | 10/1973 | Griffin et al. |
| 3,893,843 A | 7/1975 | Fry et al. |
| 3,897,210 A | 7/1975 | Gruber et al. |
| 3,948,621 A | 4/1976 | Cocuzza et al. |
| 3,963,438 A | 6/1976 | Banez |

(Continued)

FOREIGN PATENT DOCUMENTS

EP    0 583 828    2/1994

(Continued)

*Primary Examiner* — Lyle Alexander

(57) ABSTRACT

A system for recovery of a sterilant gas mixture from a sterilizer chamber is disclosed. The system includes a gas recovery tank, a sterilizer chamber in gaseous communication with the gas recovery tank and a gas recovery assembly coupled to the gas recovery tank and the sterilizer chamber. The gas recovery assembly is configured to transfer a sterilant gas mixture including at least one sterilant gas between the sterilizer chamber and the gas recovery tank. The system further includes an analyzer assembly coupled to the sterilizer chamber, the analyzer assembly including at least one sterilant gas sensor configured to detect density of the sterilant gas and a control module coupled to the analyzer assembly and to the gas recovery assembly. The control module includes at least one control module configured to determine at least one of a transfer pressure and flammability of the sterilant gas mixture as a function of the density of the sterilant gas.

14 Claims, 6 Drawing Sheets

PROCESS SCHEMATIC
100% Ethylene Oxide Sterilizer System with Sterilant Gas Recovery
Combined Function Circulation & Vacuum Booster Blower

U.S. PATENT DOCUMENTS

| | | |
|---|---|---|
| 3,964,980 A | 6/1976 | Ozero |
| 3,968,276 A | 7/1976 | Allen |
| 3,989,461 A | 11/1976 | Skocypec et al. |
| 4,028,070 A | 6/1977 | Uchii et al. |
| 4,033,617 A | 7/1977 | Cocuzza et al. |
| 4,130,393 A | 12/1978 | Fox |
| 4,249,917 A | 2/1981 | Tarancon |
| 4,301,113 A | 11/1981 | Alguire et al. |
| 4,337,223 A | 6/1982 | Kaye |
| 4,343,765 A | 8/1982 | Elston et al. |
| 4,366,125 A | 12/1982 | Kodera et al. |
| 4,370,301 A | 1/1983 | Doi et al. |
| 4,396,582 A | 8/1983 | Kodera |
| 4,430,306 A | 2/1984 | Namba et al. |
| 4,447,399 A | 5/1984 | Runnells et al. |
| 4,474,734 A | 10/1984 | Cooper |
| 4,517,159 A | 5/1985 | Karlson |
| 4,555,251 A | 11/1985 | Jonsson et al. |
| 4,576,918 A | 3/1986 | Yeung |
| 4,591,485 A | 5/1986 | Olsen et al. |
| 4,637,916 A | 1/1987 | Hennebert et al. |
| 4,639,257 A | 1/1987 | Duckett et al. |
| 4,707,334 A | 11/1987 | Gerhard |
| 4,812,292 A | 3/1989 | Joslyn |
| 4,822,563 A | 4/1989 | Joslyn |
| 4,875,909 A | 10/1989 | Kakimoto et al. |
| 4,888,155 A | 12/1989 | Posey et al. |
| 4,902,493 A | 2/1990 | Walles et al. |
| 4,954,315 A | 9/1990 | Brahmbhatt |
| 4,966,755 A | 10/1990 | Smith |
| 4,975,245 A | 12/1990 | Archer et al. |
| 4,992,247 A | 2/1991 | Foti |
| 5,114,671 A | 5/1992 | Olanders |
| 5,120,512 A | 6/1992 | Masuda |
| 5,128,101 A | 7/1992 | Boynton |
| 5,149,500 A | 9/1992 | Brahmbhatt et al. |
| 5,152,968 A | 10/1992 | Foti et al. |
| 5,209,902 A | 5/1993 | Matthews et al. |
| 5,223,217 A | 6/1993 | Frizziero |
| 5,229,071 A | 7/1993 | Meo, III |
| 5,246,663 A | 9/1993 | Ohama et al. |
| 5,261,250 A | 11/1993 | Missimer |
| 5,266,275 A | 11/1993 | Faddis |
| 5,268,144 A | 12/1993 | Heilmann et al. |
| 5,283,035 A | 2/1994 | Karthaus et al. |
| 5,286,447 A | 2/1994 | Fannin et al. |
| 5,340,538 A | 8/1994 | Zaicow et al. |
| 5,366,872 A | 11/1994 | Hird et al. |
| 5,368,815 A | 11/1994 | Kasting, Jr. et al. |
| 5,417,921 A | 5/1995 | Dove et al. |
| 5,424,034 A | 6/1995 | Hilmersson |
| 5,464,580 A | 11/1995 | Popescu et al. |
| 5,472,667 A | 12/1995 | Karthaus et al. |
| 5,474,789 A | 12/1995 | Hayami et al. |
| 5,505,908 A | 4/1996 | Nagji |
| 5,520,881 A | 5/1996 | Koestler et al. |
| 5,525,295 A | 6/1996 | Pflug et al. |
| 5,600,142 A | 2/1997 | Van Den Berg et al. |
| 5,698,011 A | 12/1997 | Chung et al. |
| 5,741,470 A | 4/1998 | Wenzler |
| 5,744,688 A | 4/1998 | Vance et al. |
| 5,792,422 A | 8/1998 | Lin et al. |
| 5,804,139 A | 9/1998 | Lin et al. |
| 5,824,239 A | 10/1998 | Jaquess |
| 5,830,409 A | 11/1998 | Childers et al. |
| 5,837,193 A | 11/1998 | Childers et al. |
| 5,843,374 A | 12/1998 | Sizer et al. |
| 5,868,997 A | 2/1999 | Wyman |
| 5,891,393 A | 4/1999 | Read et al. |
| 5,904,909 A | 5/1999 | Yates et al. |
| 5,922,277 A | 7/1999 | Donhoff et al. |
| 5,932,171 A | 8/1999 | Malchesky |
| 5,932,172 A | 8/1999 | Winks |
| 5,961,936 A | 10/1999 | Heredia |
| 5,993,739 A | 11/1999 | Lyon |
| 6,007,780 A | 12/1999 | Heredia |
| 6,019,940 A | 2/2000 | Klobucar et al. |
| 6,051,188 A | 4/2000 | Spickermann |
| 6,068,815 A | 5/2000 | Oberleitner et al. |
| 6,106,773 A | 8/2000 | Miekka et al. |
| 6,171,551 B1 | 1/2001 | Malchesky et al. |
| 6,187,266 B1 | 2/2001 | Lin et al. |
| 6,203,756 B1 | 3/2001 | Lin et al. |
| 6,207,460 B1 | 3/2001 | Kishkovich et al. |
| 6,235,240 B1 | 5/2001 | Heredia et al. |
| 6,290,906 B1 | 9/2001 | MacNeal |
| 6,331,272 B1 | 12/2001 | Sims |
| 6,379,616 B1 | 4/2002 | Sheiman |
| 6,403,359 B1 | 6/2002 | Purmal et al. |
| 6,432,357 B1 | 8/2002 | Richard et al. |
| 6,468,469 B2 | 10/2002 | Huth |
| 6,475,444 B1 | 11/2002 | Zimmermann et al. |
| 6,495,095 B1 | 12/2002 | Goeldner |
| 6,514,459 B1 | 2/2003 | Crisinel et al. |
| 6,517,775 B1 | 2/2003 | Wang et al. |
| 6,537,491 B1 | 3/2003 | Wang et al. |
| 6,541,260 B1 | 4/2003 | Pariseau et al. |
| 6,558,622 B1 | 5/2003 | Malchesky |
| 6,585,934 B1 | 7/2003 | Oberleitner et al. |
| 6,589,478 B1 | 7/2003 | Keim et al. |
| 6,596,232 B1 | 7/2003 | Lin et al. |
| 6,605,253 B1 | 8/2003 | Perkins |
| 6,617,100 B2 | 9/2003 | Purmal et al. |
| 6,638,476 B1 | 10/2003 | Elias et al. |
| 6,656,427 B2 | 12/2003 | Lin et al. |
| 6,656,472 B1 | 12/2003 | Chong et al. |
| 6,746,647 B2 | 6/2004 | Kohler et al. |
| 6,821,481 B1 | 11/2004 | Osajima et al. |
| 6,863,905 B1 | 3/2005 | Shanbrom |
| 7,008,591 B2 | 3/2006 | Kafesjian et al. |
| 7,153,471 B2 | 12/2006 | Weinberg et al. |
| 7,160,509 B2 | 1/2007 | Masaoka |
| 2002/0081228 A1 | 6/2002 | Hui et al. |
| 2003/0086820 A1 | 5/2003 | McDonnell et al. |
| 2005/0163655 A1 | 7/2005 | Lin et al. |
| 2007/0025897 A1 | 2/2007 | Rheingans et al. |
| 2007/0253865 A1 | 11/2007 | Tsutsui et al. |
| 2008/0014111 A1 | 1/2008 | Hedman |

FOREIGN PATENT DOCUMENTS

| | | |
|---|---|---|
| EP | 0 640 376 | 3/1995 |
| EP | 0 705 826 | 4/1996 |
| JP | 411145531 | 5/1999 |

PROCESS SCHEMATIC
100% Ethylene Oxide Sterilizer System with Steriliant Gas Recovery
Combined Function Circulation & Vacuum Booster Blower

SYSTEM AND METHOD FOR RECYCLING STERILANT GAS

CROSS-REFERENCE TO RELATED APPLICATION

The present application is a continuation-in-part application of U.S. patent application Ser. No. 12/637,064 filed on Dec. 14, 2009, which is a divisional application of U.S. patent application Ser. No. 11/541,358 filed on Sep. 29, 2006, now U.S. Pat. No. 7,666,369 issued on Feb. 23, 2010, the entire disclosure of all of which is incorporated by reference herein.

BACKGROUND

1. Technical Field

The present disclosure relates to a system and method for recycling sterilant gas. In particular, the present disclosure is directed to recovery and reuse of high concentration flammable sterilant gas mixtures, wherein the sterilant gas mixture is in concentrations greater than 20% by volume to a near an undiluted state of 100% by volume.

2. Discussion of Related Art

Ethylene oxide ("ETO") is a sterilizing agent well known for its effectiveness at certain gas concentrations. The objects which are to be sterilized are placed in a hermitically sealed sterilization chamber and the ETO vapor is pumped into the chamber. ETO gas is extremely flammable even in the absence of air and is, therefore, used with extreme caution in high concentrations at low pressures for sterilization purposes. Presently, high concentration ETO gas is not recycled and is only used once, afterwards the gas is then discharged to an emission control device for destruction.

One method for reusing ETO gas involves the use of a low concentration mixture of ETO and an inert gas at higher process pressures. High process pressures (e.g., up to 4 atmospheres) allow an increase in the ETO gas concentration to an acceptable milligram per liter value for effective sterilization. Mixtures having ratios of ETO to inert gas of 10/90 and 20/80 are generally used. These mixtures contain sufficient ETO concentration to assure sterilization regardless of the material being sterilized under normal temperature and at above atmospheric pressure conditions. Relative non-flammability of diluted ETO and inert gas mixtures allows for recycling of these mixtures. However, these mixtures are not as effective as higher concentrations of ETO gas.

The concentration of ETO decreases with continual use during the sterilization process since ETO is consumed in reaction with bacteria, water vapor, alcohol and the like during the sterilization process. It is possible for the ETO gas concentration to be consumed to an unsatisfactory concentration for consistent sterilization effect. Therefore, low concentration gas mixtures require processing using higher pressure rated vessels, which are more expensive. This process also involves processing the gases at above atmospheric pressures and, therefore, carries the risk of fugitive and catastrophic leakage. Consequently, in the industry today, all large ETO sterilizer chambers are designed to operate using low pressure and high concentration ETO gas. Existing sterilizers in use in the industry are not rated for the higher pressures that are required to recycle low concentration ETO gas sterilants.

It is desirable to provide a system and method for recycling sterilant gas mixtures having near 100% concentration of ETO gas to obtain maximum sterilization effectiveness while minimizing the complexity of the process and the cost of the sterilization equipment. It is desirable to provide a system that can be retrofitted to existing sterilization facilities, by the utilization of the existing sterilization process equipment and avoiding the expenses that are associated with complete system replacement.

SUMMARY

The present disclosure relates to a system and method for recycling high concentration ethylene oxide ("ETO") gas mixtures used in industrial sterilization processes. The system includes a sterilizer chamber in gaseous communication with a storage tank and a gas recovery assembly (e.g., vacuum draw). The gas recovery assembly withdraws the ETO gas to the storage tank which is adapted to store the sterilant gas at a pressure lower than the atmospheric pressure to minimize flammability thereof and fugitive leakage from the system. The ETO gas is stored in the storage tank until the sterilization chamber is to be charged with the ETO gas. It is envisioned that the storage tank may be replaced with a second sterilization chamber to allow for in tandem sterilizations. A third or forth sterilization chamber may also be connected to the system to allow gas transfer of the ETO gas from one sterilization chamber to the next chamber, thereby continually utilizing recycled gas in each sterilizer charge.

In embodiments, a system for recovery of a sterilant gas from a sterilizer chamber is disclosed. The system requires the use of an initial sterilizer evacuation and dilution with an inert purge gas to eliminate the air from the sterilizer chamber. The system includes a storage tank in gaseous communication with a sterilizer chamber via a gas recovery assembly, wherein gas can be evacuated in either direction between the sterilizer chamber and the gas storage tank utilizing the recovery system. The system utilizes an inert purge gas to dilute the residual ETO gas remaining in the sterilizer chamber to a safe nonflammable concentration, after the sterilant gas is evacuated to the storage tank. The gas recovery assembly evacuates additional diluted gas from the sterilizer chamber to the storage tank to further increase the quantity of sterilant gas being recycled.

According to another embodiment of the present disclosure a method for recovery of a sterilant gas from a sterilizer chamber is disclosed. The method includes the steps of: evacuating a sterilant gas after sterilization from a sterilizer chamber via a gas recovery assembly to a storage tank. An inert purge gas is added to the sterilizer chamber after the sterilant gas charge is withdrawn to the storage tank to reduce the flammability of the sterilant gas. Some of the purge gas is withdrawn from the sterilizer chamber and directed to the storage tank to be utilized in the enrichment of the gas mixture in the storage tank.

In embodiments, a system for recovery of a sterilant gas mixture from a sterilizer chamber is disclosed. The system includes a first sterilizer chamber in gaseous communication with a second sterilizer chamber via a gas recovery assembly. After sterilization of the first sterilizer chamber, the gas recovery assembly evacuates the sterilant gas mixture to the second sterilizer chamber, where the mixture enriched with 100% ETO to a predetermined gas concentration to sterilize objects in the second sterilizer chamber. The system also supplies an inert gas to the second sterilizer chamber after the sterilant gas mixture has been evacuated to the second sterilizer chamber, wherein the gas recovery assembly withdraws the purge gas from the first sterilizer chamber to the second sterilizer chamber to be utilized as additional replacement gas for the sterilant gas mixture in the second sterilizer chamber.

In embodiments, a system for recovery of a sterilant gas mixture from a sterilizer chamber is disclosed. The system includes a gas recovery tank, a sterilizer chamber in gaseous communication with the gas recovery tank and a gas recovery assembly coupled to the gas recovery tank and the sterilizer chamber. The gas recovery assembly is configured to transfer a sterilant gas mixture including at least one sterilant gas between the sterilizer chamber and the gas recovery tank. The system further includes an analyzer assembly coupled to the sterilizer chamber, the analyzer assembly including at least one sterilant gas sensor configured to detect density of the sterilant gas and a control module coupled to the analyzer assembly and to the gas recovery assembly. The control module includes at least one control module configured to determine at least one of a transfer pressure and flammability of the sterilant gas mixture as a function of the density of the sterilant gas.

A method for recovery of a sterilant gas mixture from a sterilizer chamber is also contemplated by the present disclosure. The method includes detecting the concentration of at least one sterilant gas present in a sterilant gas mixture; calculating a transfer pressure of the sterilant gas mixture as a function of the concentration of the at least one sterilant gas; and transferring the sterilant gas mixture from a gas recovery tank to a sterilizer chamber via a gas recovery assembly.

Another method of the present disclosure includes detecting a concentration of at least one sterilant gas present in a sterilant gas mixture; calculating at least one of a transfer pressure and flammability of the sterilant gas mixture as a function of the concentration of the at least one sterilant gas and a target sterilant gas concentration; and transferring the sterilant gas mixture from a gas recovery tank to a sterilizer chamber via a gas recovery assembly.

BRIEF DESCRIPTION OF THE DRAWINGS

Various embodiments of the present disclosure are described herein with reference to the drawings wherein.

DETAILED DESCRIPTION

Particular embodiments of the present disclosure are described herein below with reference to the accompanying drawings. In the following description, well-known functions or constructions are not described in detail to avoid obscuring the present disclosure in unnecessary detail.

Figure 1:
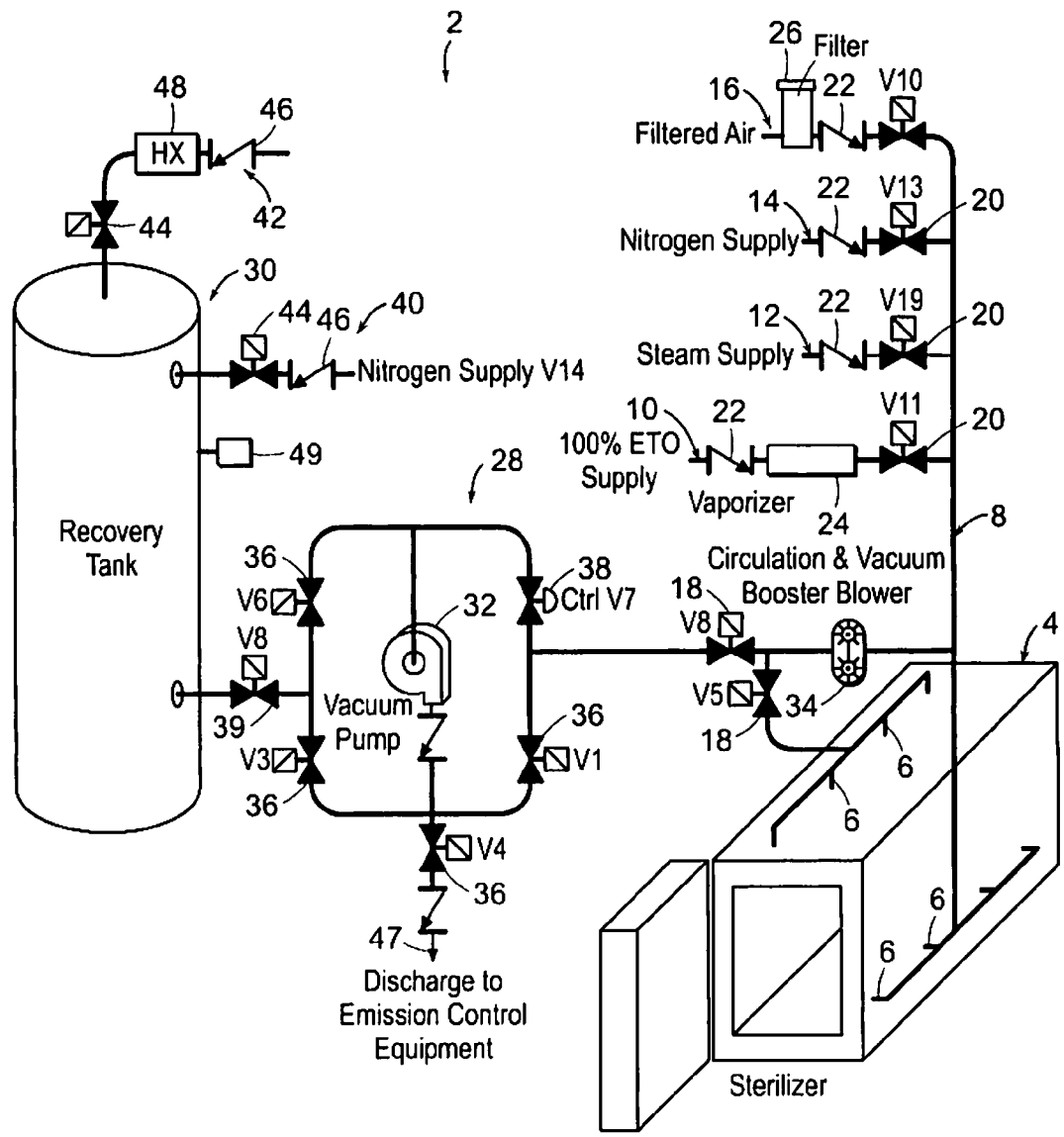
FIG. 1 is a schematic view of an embodiment of a sterilant gas recycling system according to the present disclosure.

Referring now to FIG. 1, a recycling system 2 in accordance with the principles of the present disclosure is illustrated. The recycling system 2 is adapted to recapture and reuse a sterilant gas, such as ethylene oxide ("ETO"). Those skilled in the art will appreciate that the present disclosure is not limited to recycling of ETO and that other suitable gases selected for their sterilization properties may be used.

The recycling system 2 includes a sterilizer chamber 4 which is configured to be hermetically sealed once objects in need of sterilization are placed therein to prevent gaseous flow between the sterilizer chamber 4 and the outside. The sterilizer chamber 4 includes one or more gas inlets 6 connected to a gas supply line 8. The gas supply line 8 includes an ETO supply 10, a steam supply 12, a purge gas supply 14, and a filtered air supply 16. The gas supply line 8 also includes pressure actuated shut-off valves 18 in communication with piping leading to the gas inlets 6. Each of the supplies 10, 12, 14 and 16 include a secondary pressure actuated shut-off valve 20 and a check valve 22 which allows for unidirectional flow of gasses into the sterilizer chamber 4.

The ETO supply 10 provides a direct source of ETO gas to the sterilizer chamber 4 for the initial supply of ETO gas prior to commencement of recycling process as well as for any refortification of the ETO gas. The ETO supply 10 includes a heat exchanger 24 that is used to convert (e.g., vaporize) the liquid 100% ETO from the supply drums (not explicitly shown) to vapor state. The steam supply 12 provides water steam in multi-stage sterilization processes. The purge gas supply 14 provides a purge gas (e.g., nitrogen, carbon dioxide, etc.) to the ETO gas within the sterilizer chamber 4 to decrease the flammability of the ETO gas and to purge any remnants of the ETO gas after the first vacuum draw as discussed in more detail below. The air supply 16 includes an air vent 26 and provides a supply of filtered air which is used to fill the sterilizer chamber 4 after the ETO gas has been withdrawn to return the sterilizer chamber 4 to normal atmospheric conditions.

The recycling system 2 also includes a gas recovery assembly 28 which is in gaseous communication with the sterilizer chamber 4 and a recovery storage tank 30. The gas recovery assembly 28 transfers the ETO gas from the sterilizer chamber 4 into the recovery tank 30. The gas recovery assembly 28 includes a vacuum pump 32 and a circulation blower 34. The pump 32 is connected to a plurality of pressure controlled shut off valves 36 which control the direction of the gas flow through the gas recovery assembly 28. In addition, the gas recovery assembly 28 includes a manual control valve 38 which allows to terminate gas flow therein (e.g., emergency situations). The circulation blower 34 can be configured to facilitate gas flow out of the sterilizer chamber 4 by functioning as a vacuum booster blower in series prior to the vacuum pump 32, to effect a deeper recovery vacuum from the sterilizer chamber, which will maximize the quantity of sterilant gas recovered.

Piping connecting the recovery tank 30 to the gas recovery assembly 28 includes a pressure controlled shut-off valve 39. The recovery tank 30 also includes a purge gas supply 40 and an ETO supply 42. Each of the supplies 40 and 42 include a pressure controlled shut-off valve 44 and a check valve 46. Further, the ETO supply 42 includes a heat exchanger 48 to vaporize liquid ETO. The purge and ETO gas supplies 40 and 42 provide the storage tank 30 with nitrogen and ETO gases respectively such that the ratio of the gases can be adjusted during the recycling process.

Since the sterilant gas being used is high concentration ETO gas, the sterilization is accomplished at approximately atmospheric pressure to minimize flammability of the gas. It is also envisioned that the sterilizer chamber 4 and the storage tank 30 as well as other components of the recycling system 2 are rated for operation with flammable gas mixtures. During operation, the ETO gas is mixed with the purge gas in desired concentrations in the recovery tank 30 through the purge and ETO gas supplies 40 and 42 to form a sterilant gas mixture. Once objects are loaded into the sterilizer chamber 4, the chamber 4 is evacuated to remove air. Purge gas is added to the sterilizer chamber 4 through the purge gas supply 14 and the sterilizer chamber 4 is again evacuated. This may be repeated a few times to ensure that all air is removed from the sterilizer chamber 4. Thereafter, the sterilant gas mixture is pumped into the sterilizer chamber 4 along with pure ETO gas and purge gas to achieve the desired gas ratio. The circulation blower 34 is activated to mix the gases within the sterilant chamber 4.

After the sterilant gas mixture has been in the sterilizer chamber 4 for a sufficient amount of time to sterilize its contents, the vacuum pump 32 evacuates the sterilizer chamber 4 and transfers to gas mixture back to the recovery tank 30. As the sterilant gas mixture is transferred, the pressure within the sterilizer chamber 4 is lowered to substantially vacuum conditions given structural limitations of the sterilizer chamber 4 and capacity of the vacuum pump 32. The recovery tank 30 has a larger volume than the sterilizer chamber 4 (e.g., 110% of the volume of the sterilizer chamber 4) such that the pressure of transferred ETO gas therein is lower than the pressure of the gas within the sterilizer chamber 4 (i.e., atmospheric pressure). Since throughout the sterilization process all gases are stored and handled at pressures which are less than atmospheric, the environmental risk of fugitive gas leakage is drastically reduced.

After the recovery vacuum draw has been completed, the pressure in the sterilizer chamber 4 is increased to approximately 3 PSI by adding a purge gas (e.g., nitrogen gas) from the purge gas supply 14. A second stage recovery vacuum draw is performed to recover gas from the sterilizer chamber 4 until the recovery tank 30 has achieved the target pressure capacity, thereby mixing the ETO gas with the purge gas. The sterilizer chamber 4 is then pressurized to atmospheric pressure using purge gas from the purge gas supply 14 or air from the filtered air supply 16, if the contents of the sterilizer chamber 4 are non-flammable. Thereafter, subsequent vacuum draws via the vacuum pump 32 are discharged to standard emission control equipment (not specifically shown) through a discharge vent 47.

The air is purged by the initial vacuum draws and displaced with inert dilution gas so that the percentage of air in the gas mixture does not exceed 20%. If the sum of the ETO percentage and the inert dilution gas is less than 80%, then gas is vented off to the emission control device and replaced with pure 100% dilution gas.

The ETO gas mixture is stored in the recovery tank 30 at atmospheric pressure and is transferred back to the sterilizer chamber 4 during the next sterilization cycle via the vacuum pump 32. Prior to starting a sterilization process cycle, the sterilant gas mixture in the recovery tank is sampled and analyzed using a process gas analyzer 49. The analyzer 49 can be installed at a port of a pressure vessel (e.g., recovery tank 30, sterilizer chamber 4, etc.) or can be connected to multiple vessels through a valve network of tubing. The analyzer 49 can utilize gas chromatography, or infrared spectral analysis, to obtain reliable measurements of the ETO gas and the purge gas amounts. It is desirable to know the percentages of the gas components to ensure process safety. More specifically, concentration of gas components allows for calculation of the flammability of the process gas mixture and sterilization effect on the objects in the sterilizer chamber 4.

The sterilization process according to the present disclosure is configured to operate via variety of validated ETO gas concentrations. The gas concentration is measured in the sterilizer chamber 4 during the sterilization gas exposure dwell. The pressure is then be adjusted according to the ideal gas law to control the gas density that the objects being sterilized are exposed. Additional ETO gas is provided through the ETO gas supply 10 if the gas mixture within the sterilizer chamber 4 needs to be refortified. It is envisioned that ETO gas recovery is about 85% of the original charge, wherein about 15% of the ETO gas is lost due to product absorption, glycol conversion, vacuum pull down limitations, etc.

Figure 2:
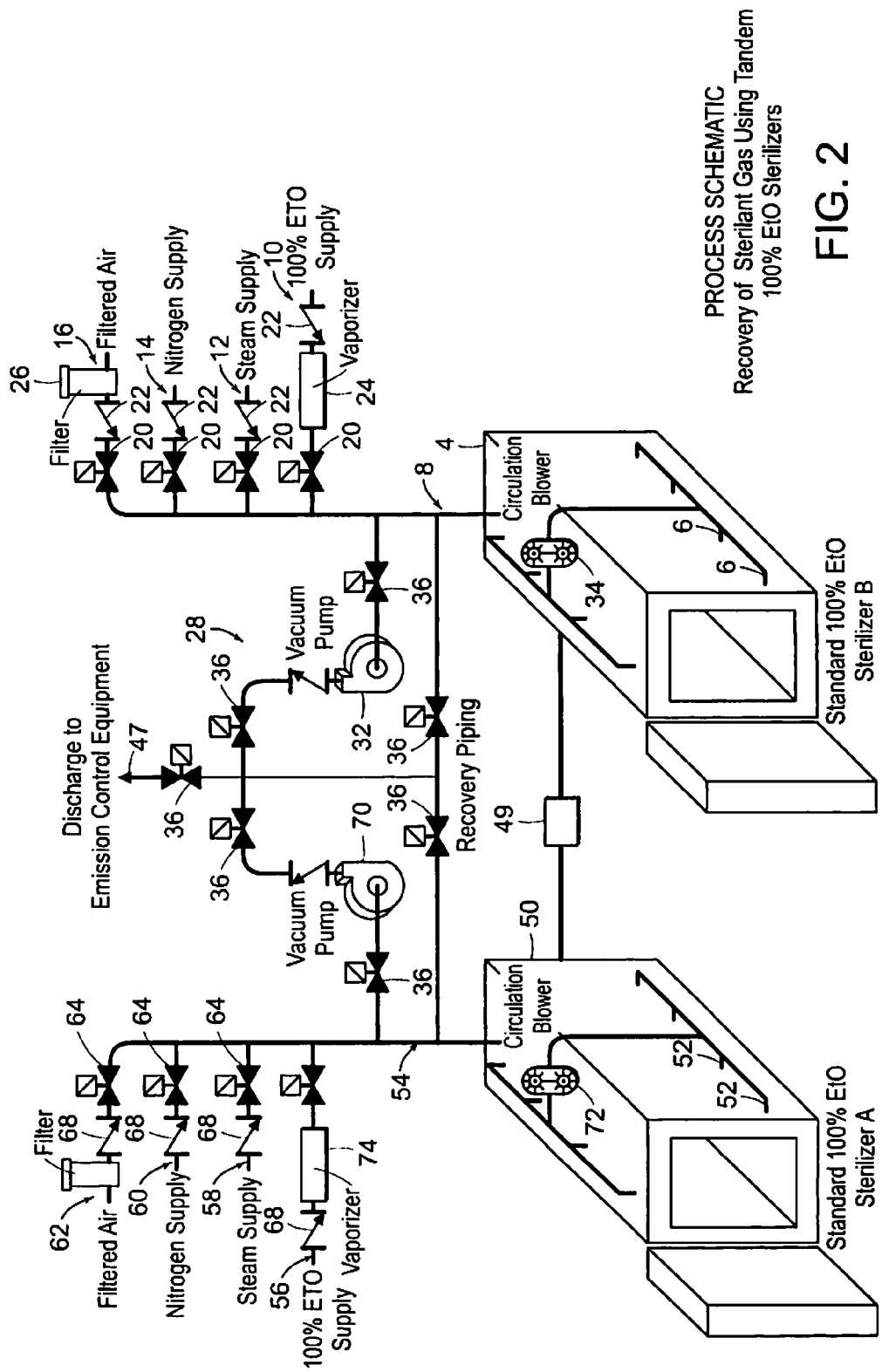
FIG. 2 is a schematic view of another embodiment of a sterilant gas recycling system according to the present disclosure.

Referring to FIG. 2, another embodiment of the recycling system 2 is illustrated, wherein the storage tank 30 is replaced with a second sterilizer chamber 50 which is in gaseous communication with the first sterilizer chamber 4. The sterilizer chamber 50 is configured to be hermetically sealed and includes similar components as the sterilizer chamber 4. In particular, the sterilizer chamber 50 includes one or more gas inlets 52 connected to a gas supply line 54 which includes an ETO gas supply 56, a steam supply 58, a purge gas supply 60, and a filtered air supply 62. Each of the supplies 56, 58, 60 and 62 include a secondary pressure actuated shut-off valve 64 and a check valve 68 which allows for unidirectional flow of gasses into the sterilizer chamber 50.

The gas recovery assembly 28 transfers the ETO gas between the sterilizer chamber 4 and the sterilizer chamber 50. The gas recovery assembly 28 includes the vacuum pump 32, the circulation blower 34, a second vacuum pump 70 and the circulation blower 72. The pumps 32 and 70 are connected to a plurality of pressure controlled shut off valves 36 which control the direction of the gas flow through the gas recovery assembly 28. The circulation blowers 34 and 72 are configured to facilitate gas flow between the sterilizer chambers 4 and 50.

During operation, the ETO gas is mixed with the purge gas in desired concentrations in the sterilizer chamber 50 through the ETO and purge gas supplies 56 and 60 to form a sterilant gas mixture. Once objects are loaded into the sterilizer chamber 4, one or more vacuum draws are performed using purge gas to fill the sterilizer chamber 4. Thereafter, the sterilant gas mixture is pumped into the sterilizer chamber 4 along with pure ETO gas and purge gas to achieve the desired gas ratio. The circulation blower 34 is activated to mix the gases within the sterilant chamber 4.

After the sterilant gas mixture has been in the sterilizer chamber 4 for a sufficient amount of time to sterilize its contents, the vacuum pump 32 evacuates the sterilizer chamber 4 and transfers to gas mixture back to the sterilizer chamber 50. As the ETO gas is transferred, the pressure within the sterilizer chamber 4 is lowered to substantially vacuum conditions given structural limitations of the sterilizer chamber 4 and capacity of the vacuum pump 32. The sterilizer chamber 50 has a substantially same volume as the sterilizer chamber 4 such that the pressure of transferred ETO gas therein is the same as the pressure of the gas within the sterilizer chamber 4 (i.e., atmospheric pressure).

After the recovery vacuum draw has been completed, the pressure in the sterilizer chamber 4 is increased to approximately 3 PSI by adding a purge gas (e.g., nitrogen gas) from the purge gas supply 14. A second stage recovery vacuum draw is performed to recover gas from the sterilizer chamber 4 until the sterilizer chamber 50 has achieved the target pressure capacity, thereby mixing the ETO gas with the purge gas. The sterilizer chamber 4 is then pressurized to atmospheric pressure using purge gas from the purge gas supply 14 or air from the filtered air supply 16, if the contents of the sterilizer chamber 4 are non-flammable. Thereafter, subsequent vacuum draws via the vacuum pump 32 are discharged to standard emission control equipment (not specifically shown) through the discharge vent 47.

Additional ETO gas is provided to the sterilizer chamber 50 through the ETO gas supply 56 if the gas mixture within the sterilizer chamber 50 needs to be refortified. A heat exchanger 74 vaporizes liquid ETO into gaseous state. The recovered ETO gas mixture is kept within the sterilizer chamber 50 at atmospheric pressure and is transferred back to the sterilizer chamber 4 during the next sterilization cycle once the sterilizer chamber 4 is prepared for another sterilization load.

Figure 3:
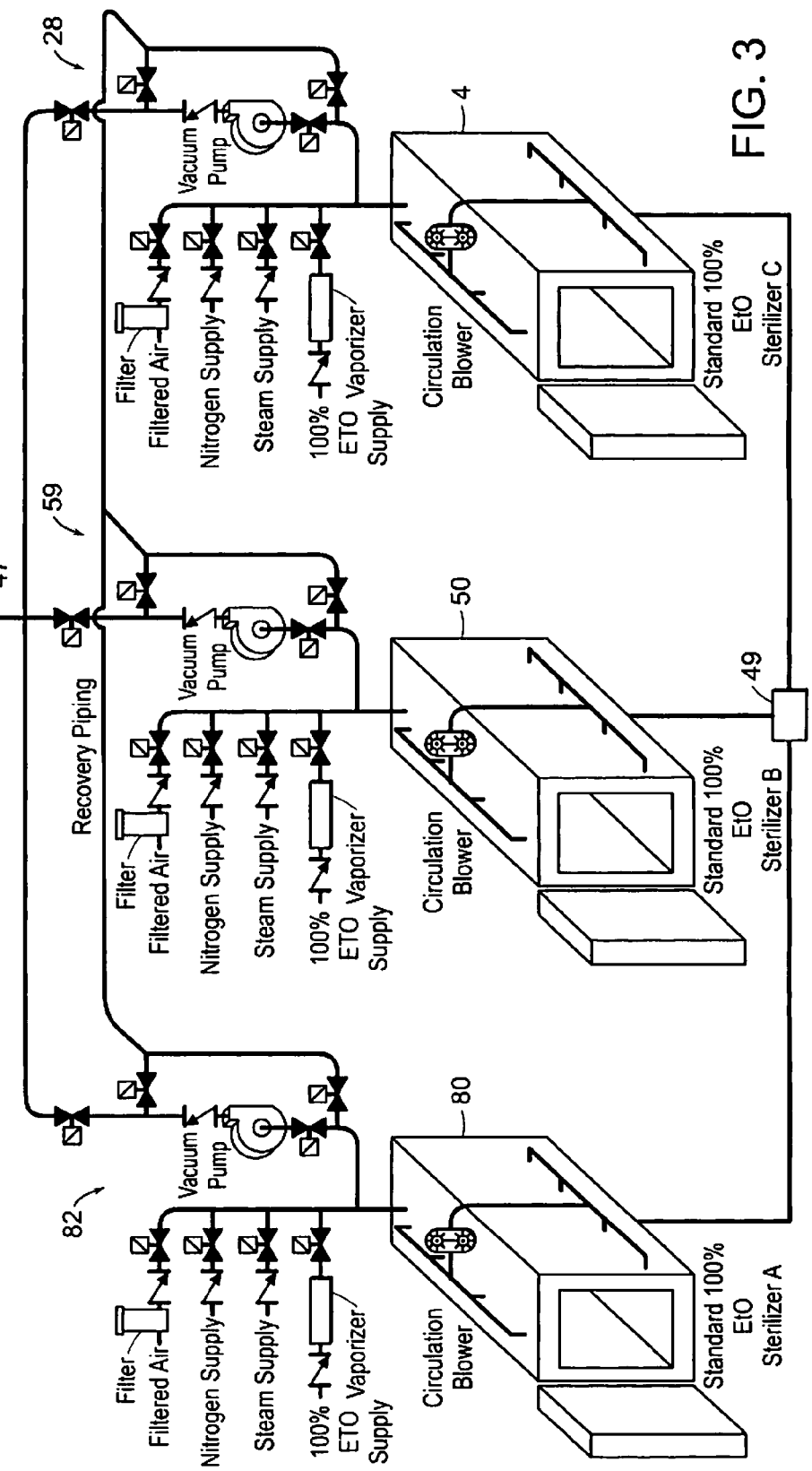
FIG. 3 is a schematic view of another embodiment of a sterilant gas recycling system according to the present disclosure.

Those skilled in the art will appreciate that multiple sterilization chambers may be connected to each other to facilitate in tandem sterilization, thereby recycling the ETO gas by transferring the gas from one chamber or storage tank to another. FIG. 3 shows a further modification of three sterilizer chambers 4, 50 and 80 connected in tandem as a single recovery system. The sterilant gas mixture is transferred from one sterilizer chamber to the next during the sterilization process. The sterilizer chamber 80 is connected to a recovery system 80 which is in gaseous communication with a recovery system 59 of the sterilizer chamber 50 and the recovery system 28 of the sterilizer chamber 4. Those skilled in the art will readily appreciate that the recovery systems 4, 59 and 80 and the sterilizer chambers 4, 50 and 80 include similar components as discussed above with embodiments shown in FIGS. 1-2 (e.g., vacuum pumps, filtered air, nitrogen, steam and ETO gas supplies, etc.). This arrangement is desirable when objects to be sterilized need to spend extended periods of time in the sterilizer chambers, e.g., for humidification and temperature warming prior to gas exposure, extended product off-gassing time in the chamber, etc. The use of three or four sterilizer chambers operating in a staggered manner may also be desirable to sterilize certain dense types of product.

Figure 4:
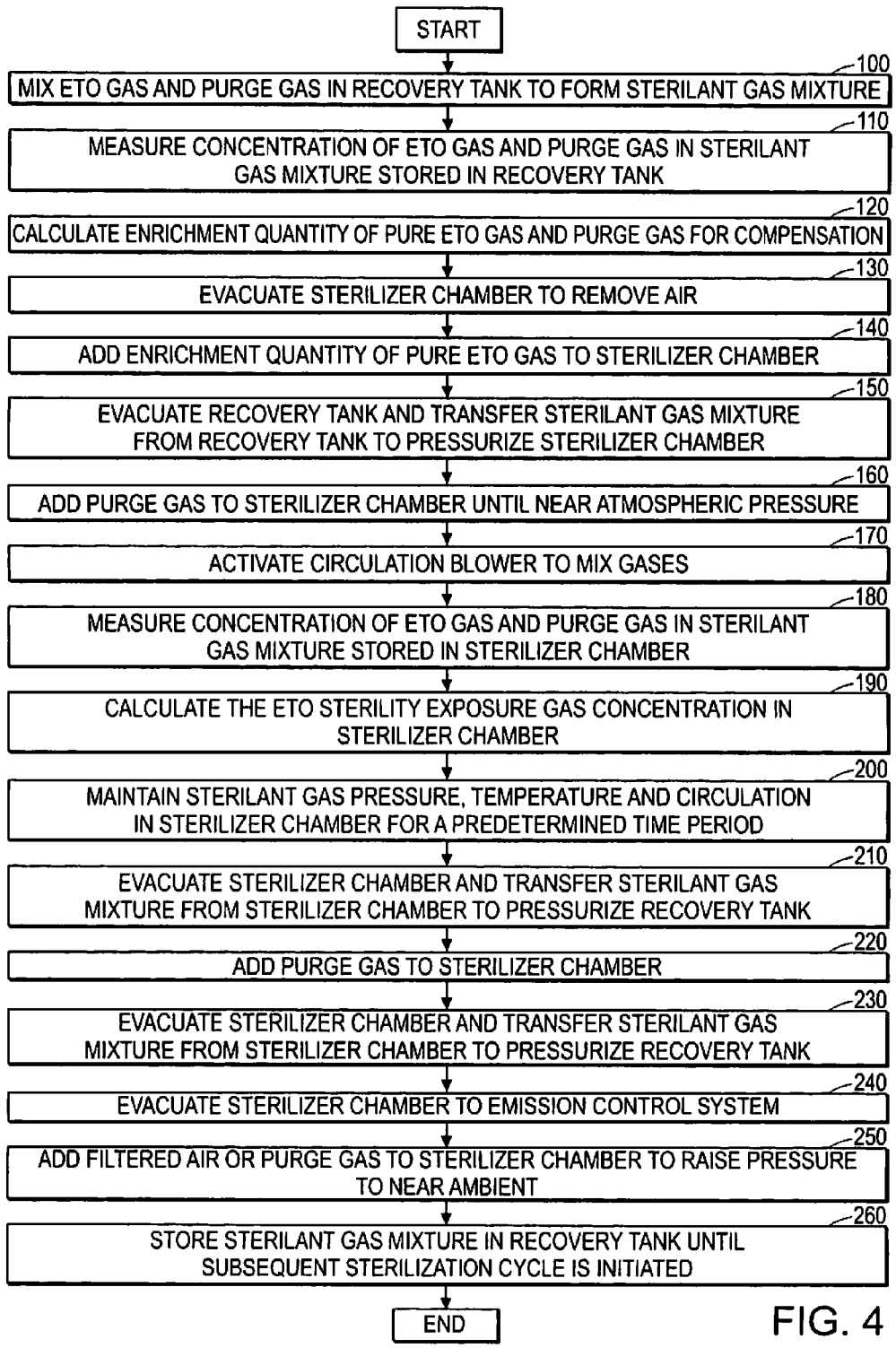
FIG. 4 is a flow diagram of a method for recycling sterilant gas according to the present disclosure.

FIG. 4 shows a flow chart of a method for recycling sterilant gas according to the present disclosure. In step 100, ETO gas and purge gas are mixed in desired proportions to form a sterilant gas mixture in the recovery tank 30 or a sterilizer chamber, if an in tandem system is being used. In step 110, concentration of the ETO and purge gases in the sterilant gas mixture is measured using the gas analyzer 49 to ensure a safe and effective sterilant gas composition. In step 120, enrichment quantities for ETO and purge gases are calculated to ensure that the concentration of ETO gas and pressure within the sterilizer chamber 4 is at a predetermined set point. In step 130, the sterilizer chamber 4 is evacuated and purged of air using one or more vacuum draws and a dilution via purge gas. In step 140, undiluted ETO gas is added into the sterilizer chamber 4 to provide an initial charge of gas into the sterilizer based on the calculations of step 120.

In step 150, the sterilant gas mixture in the recovery tank 30 is evacuated into the sterilizer chamber 4. In step 160, the purge gas is added to the sterilizer chamber 4 to raise the chamber pressure to near atmospheric pressure to minimize the risk of air leaking into the chamber based on the calculations of step 120. In step 170, the circulation blower 34 is activated to mix the gases added into the sterilization chamber. In step 180, concentration of ETO and purge gases in the sterilant chamber 4 is measured. In step 190, ETO gas sterility exposure gas concentration (e.g., milligrams per liter) is calculated. In step 200, the gas mixture is circulated and is maintained at a predetermined temperature and pressure within the sterilizer chamber 4. The sterilant gas mixture is kept in the sterilizer chamber 4 for a sufficient amount of time, at validated temperature and predetermined concentration parameters to sterilize its contents. In step 210, the sterilizer chamber 4 is evacuated to transfer the sterilant gas mixture back to the recovery tank 30 to pressurize the recovery tank 30 at or near the atmospheric pressure. After the recovery vacuum draw has been completed, in step 220, purge gas (e.g., nitrogen gas) from the purge gas supply 14 is added to the sterilizer chamber 4. This increases the pressure in the sterilizer chamber 4 to approximately 3 PSI. In step 230, a second stage recovery vacuum draw is performed to recover gas from the sterilizer chamber 4 until the sterilizer chamber 50 or the storage tank 30 has achieved the target pressure capacity. In step 240, once the recovery tank 30 is at the desired pressure set point, the contents of the sterilizer chamber 4 are evacuated to the emission control system. In step 250, the sterilizer chamber 4 is pressurized to atmospheric pressure using purge gas from the purge gas supply 14 or air from the filtered air supply 16. Optionally, subsequent vacuum draws are discharged to standard emission control equipment through the discharge vent 47. In step 260, the mixture of ETO gas and the purge gas is stored in the recovery tank 30 or the sterilization chamber 50. The recovered ETO gas mixture is kept within the recovery tank 30 or the sterilizer chamber 50 at near atmospheric pressure and is transferred back to the sterilizer chamber 4 during the next sterilization cycle once the sterilizer chamber 4 is prepared for another sterilization load.

Figure 5:
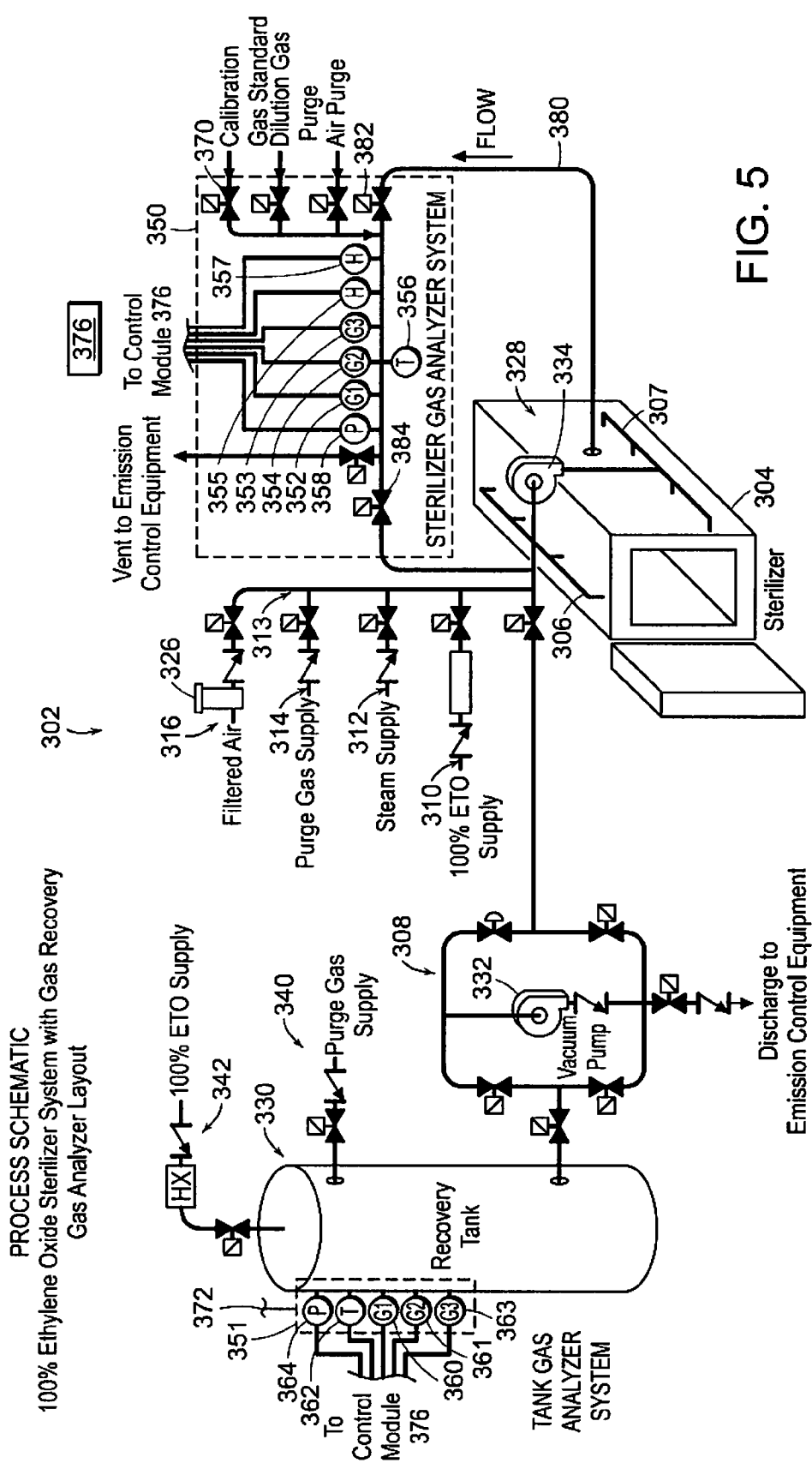
FIG. 5 is a schematic view of an embodiment of a sterilant gas recycling system according to the present disclosure.

Referring now to FIG. 5, another embodiment of a sterilant gas recycling system 302 in accordance with the present disclosure is illustrated. The recycling system 302 is adapted to recapture and reuse a sterilant gas (e.g., ETO). The recycling system 302 is similar to the recycling system 2 of FIG. 1, and includes a sterilizer chamber 304 and a recovery storage tank 330 coupled thereto via a gas recovery assembly 308. Each of the sterilizer chamber 304 and the recovery storage tank 330 includes a jacket hydronic heating system for adjusting the temperature of the sterilant gas mixture therein. Other heating systems within the purview of those skilled in the art may also be utilized.

The recovery tank 330 also includes a purge gas supply 340 and an ETO supply 342. The purge and ETO gas supplies 340 and 342 provide the storage tank 330 with the purge gas and ETO, respectively, such that the ratio of the gases can be adjusted during the recycling process. During operation, the ETO gas is mixed with the purge gas in desired concentrations in the recovery tank 330 through the purge and ETO gas supplies 340 and 342 to form and/or refortify a sterilant gas mixture.

The sterilizer chamber 304 is configured to be hermetically sealed and includes one or more gas inlets 306 and outlets 307 connected to a gas circulation assembly 328, which is in turn coupled to the gas recovery assembly 308. The gas recovery assembly 308 is in gaseous communication with the sterilizer chamber 304 and the recovery storage tank 330. The gas recovery assembly 308 transfers the sterilant gas mixture between the sterilizer chamber 304 into the recovery tank 330. The gas circulation assembly 328 circulates the sterilant gas mixture through the sterilizer chamber 304.

The gas inlets 306 and outlets 307 are coupled to a gas supply line 313, which includes an ETO supply 310, a steam supply 312, an inert purge gas supply 314, and a filtered air supply 316. The ETO supply 310 provides a direct source of ETO gas to the sterilizer chamber 304 for the initial supply of ETO gas prior to commencement of the transfer process as well as for any refortification of the ETO gas. The steam supply 312 provides water steam in a multi-stage sterilization processes. The purge gas supply 314 provides an inert purge gas (e.g., nitrogen, carbon dioxide, etc.) to the ETO gas within the sterilizer chamber 304 to decrease the flammability of the ETO gas and to purge any remnants of the ETO gas after the first vacuum draw as discussed above. The air supply 316 includes an air vent 326 and provides a supply of filtered air which is used to fill the sterilizer chamber 304, after the ETO gas has been withdrawn to return the sterilizer chamber 304 to normal atmospheric conditions.

The gas recovery assembly 308 also includes a vacuum pump assembly 332 that is connected to a plurality of pressure controlled shut off valves that control the direction of the gas flow through the gas circulation assembly 328. The vacuum pump assembly 332 may include a plurality of vacuum pumps coupled in series to provide for increased pressure, to effect a deeper recovery vacuum from the sterilizer chamber 304 thereby maximizing the amount of the sterilant gas mixture transferred between the sterilizer chamber 304 and the recovery tank 330.

The gas circulation assembly 328 includes one or more circulation fans 334. The gas circulation assembly 328 also includes shut-off valves in communication with piping leading to the gas inlets 306 and outlets 307, respectively. The circulation fans 334 are coupled to the gas inlets 306 and outlets 307 and circulate the sterilant gas mixture within the sterilizer chamber 304 during the sterilization process. This provides for more efficient contact between the sterilization gases and the objects. The gas circulation assembly 328 and the gas recovery assembly 308 may include a manual control valve which allows one to terminate gas flow therein (e.g., in emergency situations).

The system 302 also includes a first analyzer assembly 350 coupled to the sterilizer chamber 304 and a second analyzer assembly 351 coupled to the recovery tank 330. The first analyzer assembly 350 is coupled to the sterilizer chamber 304 via analyzer piping 380 having analyzer isolation valves 382 and 384, which are opened during exposure to allow for continuous analysis of the sterilant gas mixture present in the sterilizer chamber 304.

The analyzer assembly 350 includes first and second sterilant gas sensors 352 and 354, a first inert gas sensor 353, first and second relative humidity sensors 355 and 357, a first temperature sensor 356, and a first pressure sensor 358. The dual sterilant gas sensors 352 and 354 provide redundant measurements of the sterilant gas within the sterilant chamber 304. The first inert gas sensor 353 measures the concentration of the inert dilution gas. The first and second humidity sensors 355 and 357 provide redundant measurements of the water content of the gas mixture within the sterilizer chamber 304. The first temperature sensor 356 and first pressure sensors 358 measure temperature and pressure, respectively, and are used to compensate for the measurements of the individual gas sensors 352, 353, and 354.

The second EO analyzer assembly 351 located on the recovery tank 330 includes third and fourth sterilant gas sensors 360 and 361, a second inert gas sensor 363, a second temperature sensor 362, and a second pressure sensor/transmitter 364. The dual sterilant gas sensors 360 and 361 provide redundant measurements of the sterilant gas within the recovery tank 330. The second inert gas sensor 363 measures the concentration of the inert dilution gas. The second temperature sensor 362 and second pressure sensor 364 measure temperature and pressure, respectively, and are used to compensate for the measurements of the individual gas sensors 360, 361, 363.

Each of the first and second analyzer assemblies 350 and 351 includes a calibration connection 370 and 372, respectively. The calibration connections 370 and 372 are used to couple to a portable calibration gas source (e.g., gas cylinder). The calibration gas mixture may include from about 10% to about 70% ETO, and from about 30% to about 90% of purge gas, in embodiments, from about 20% to about 60% ETO, and from about 40% to about 80% of purge gas. Since a portion of the sterilant gas mixture is air, air is replaced with nitrogen to render the calibration gas mixture non-explosive.

The recycling system 302 also includes a control module 376 coupled to the first and second analyzer assemblies 350 and 351. The control module 376 may be a computing device having a logic controller (e.g., digital signal processor, microprocessor, etc.) for accepting sensor inputs from the first and second analyzer assemblies 350 and 351. In embodiments, the control module 376 may be coupled to the sensors of the analyzer assemblies 350 and 351 either via wires or wirelessly. The control module 376 may also include memory (e.g., read only memory) for storing various software instructions readable by the logic controller for analyzing and processing sensor inputs. In embodiments, the logic controller also includes a variety of outputs for coupling to the recycling system 302 and/or other output devices (e.g., video monitors, audio alarms, printers, etc.). In particular, the logic controller may be coupled to various control valves of the recycling system 302 and may open, close, or otherwise adjust the flow of gases through the recycling system 302 based on the software instructions and/or sensor inputs.

The sensors of the analyzer assemblies 350 and 351, namely, first, second and third sterilant gas sensors 352, 354, 360, generate a current signal from about 4 milliamps (mA) to about 20 mA, which is then converted by the logic controller of the control module 376 into gas concentration (e.g., dividend of volume of specific gas and total system volume total, or molar amount of the specific gas and the total molar amount of the mixture) of the ETO in the sterilant gas mixture (mg/L) using the following scaling formula (I):

$$r_{actual} = \frac{(gas_{md} - 4) * 1000}{16} \quad (I)$$

In formula (I), $gas_{mA}$ denotes gas sample value in milliamps (mA) and $r_{actual}$ denotes actual concentration of ETO. The lowest range value (e.g., 4 mA) is subtracted from the gas sample value, $gas_{mA}$, and is then multiplied by the conversion factor (e.g., 1000) and scaled using a desired scaling factor (e.g., 16). The listed factors and constants are provided for illustrative purposes only and may be substituted by other values to achieve desired scaling and/or conversion.

The control module 376 also determines various characteristics of the sterilant gas mixture based on gas concentration and atmospheric conditions (e.g., temperature and pressure readings) using ideal gas law formulas. In embodiments, the control module determines ETO percentage in the sterilant gas mixture using the gas concentration of ETO from formula (I) and the following formula (II):

$$ETO\ \% = \frac{(r_{actual} * 0.0000625) * (T + 460) * 35.08}{P * 144} * 100 \quad (II)$$

In formula (II), T is the temperature and P is pressure within either the sterilizer chamber 304 or the storage tank 330, as detected by the temperature sensors 356 and 362 and/or the pressure sensors 358 and 364, respectively. The constant of 144 is an area unit conversion for converting square inches to square feet and 460 is a temperature unit conversion from Farenheight to Rankine. The constants, 0.0000625 and 35.08 are provided to simplify formula (II) and are derived from the ideal gas law formula (III) that is listed below:

$$\%\ Concentration = d * R * T / P \quad (III)$$

In formula (III), d is density expressed as mg/L, R is the universal gas constant that is 1545.33/molar weight, expressed as feet (ft)*pound force (lbf/pound-mass (lbm) *temperature in Rankine (° R), which for ETO is 44.05 lbm/mole, T is temperature expressed in ° R, and P is pressure expressed in pounds per square inch absolute (psia) as detected by the temperature sensor 356 and the pressure sensor 358, respectively, within the sterilizer chamber 304.

The control module 376 is also configured to calculate a desired transfer pressure value ($P_{desired}$), namely the pressure within the sterilizer chamber 304 needed to achieve the target gas concentration of ETO (e.g., $r_{desired}$ of 450 mg/L). The control module 376 also calculates the flammability of the sterilant gas mixture at the desired concentration and the required transfer pressure. Flammability is estimated using a flammability table that provides for flammability values of different gas mixtures at various pressures. The transfer pressure is calculated using the following formula (IV):

$$P_{desired} = \frac{Density_{ETO} * R_{ETO} * (T + 460)}{ETO\% * 144} + P \quad (IV)$$

$R_{ETO}$ is a specific gas constant that is the dividend of the gas constant R and molecular weight of ETO, which for ETO is 44.05 lbm/mole. $Density_{ETO}$ is the density (e.g., dividend of a mass of specific gas and total system volume) of the ETO which is calculated using the following formula (V):

$$Density_{ETO} = r_{desired}/16016.9 \quad (V)$$

In formula (V), $r_{desired}$ denotes desired concentration of ETO. The 16016.9 is provided to simplify formula (IV) and is derived from the ideal gas law formula (VI) that is listed below.

$$\text{Gas Density} = m/V = P/(R*T)*x \quad (VI)$$

In formula (VI), m is mass expressed as pound-mass (lbm), V is volume expressed as cubic feet (ft³), R is the universal gas constant that is 1545.33/molar weight, expressed as feet (ft) *pound force (lbf)/pound-mass (lbm)*temperature in Rankine (° R), which for ETO is 44.05 lbm/mole, T is temperature expressed in ° R, P is pressure expressed in pounds per square inch (psia), and x is the concentration of gas in mixture expressed as percent.

Figure 6:
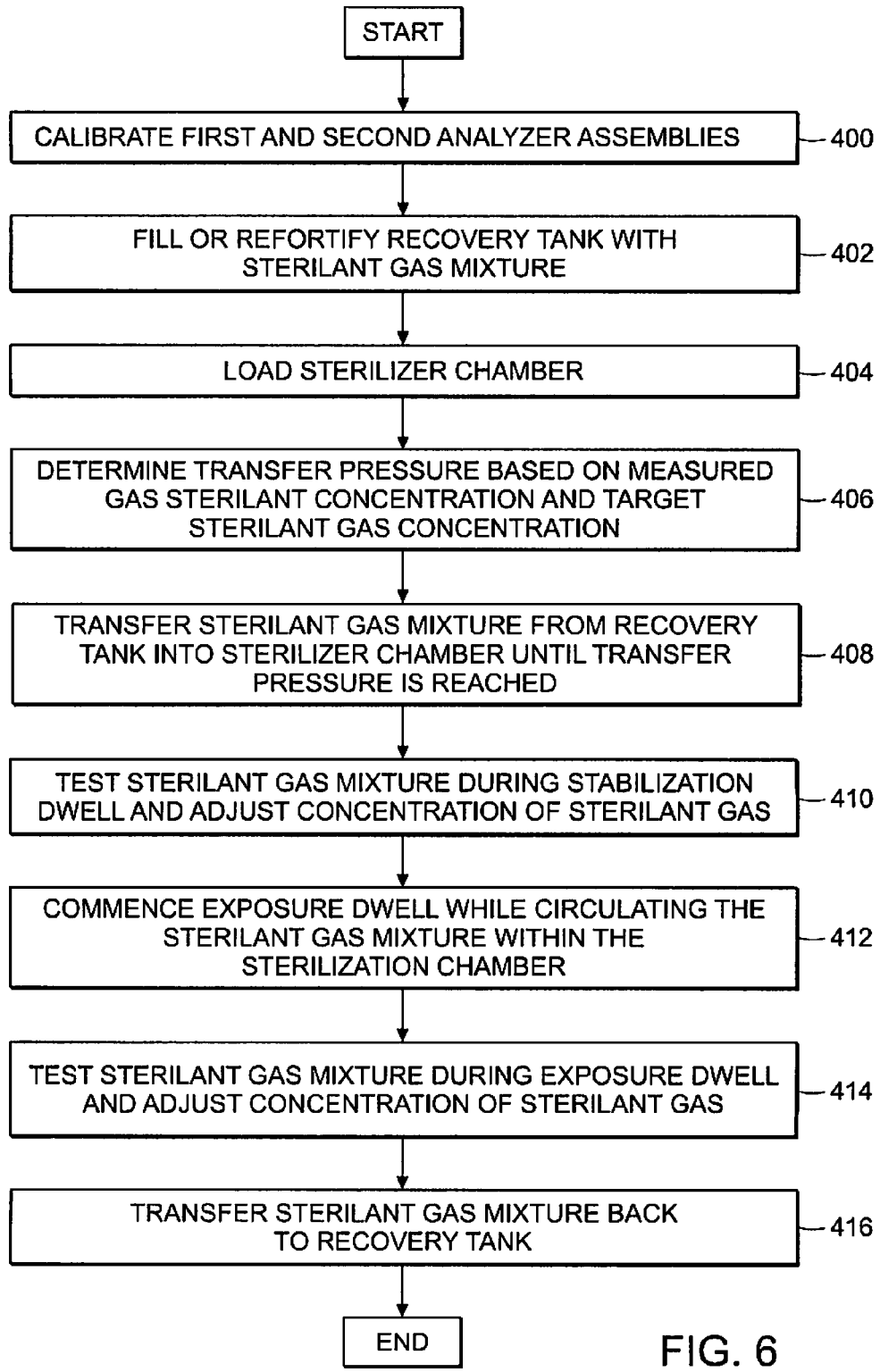
FIG. 6 is a flow diagram of a method for recycling sterilant gas according to the present disclosure.

FIG. 6 illustrates a method of operation of the recycling system 302 of FIG. 5. In step 400, the first and second analyzer assemblies 350 and 351 are calibrated by coupling the calibration gas source to each of the assemblies 350 and 351 and sampling the calibration gas. The sensors of the assemblies 350 and 351 are then adjusted to reflect the stated gas concentration of the calibration gas source.

In step 402, the recovery tank 330 is filled and/or refortified with a sterilant gas mixture having a desired amount of ETO, $CO_2$, $N_2$ and other atmospheric gases depending on the whether the recovery tank 330 has been charged by a previous sterilization processing cycle. The sterilant gas mixture may include from about 30% to about 60% of ETO, from about 30% to about 60% of purge gas, and about 10% of air, with the total volume of the gas mixture being about 100%.

The recovery tank 330 may be sized to about 110% of the volume of the sterilizer chamber 304, to allow for extra gas demand that may occur in the sterilizer chamber 304 (e.g., due to product gas absorption). Pressures in the sterilizer chamber 304 may be from about a near-vacuum during vacuum purges (e.g., from about 0.5 psia to about 2.5 psia, in embodiments, from about 0.6 psia to about 2.4 psia) to about atmosphere pressure (e.g., about 14.0 psia) when the sterilizer chamber 304 is fully charged with sterilant gas mixture. Maintaining the pressure of the sterilizer chamber 304 at near-atmospheric pressure limits the potential for fugitive leakage to the facility. Also, the potential of air leaking into the sterilizer chamber 304 and creating a flammable gas mixture is limited by the near to atmosphere pressure differential. Pressures in the recovery tank 330 when it is fully charged (e.g., when the sterilizer chamber 304 is not charged with sterilant gas mixture) may also be about near-atmosphere pressure (e.g., 14.0 psia) to prevent fugitive leakage and air infiltration. In embodiments, the pressure within the recovery tank 330 may be drawn down to about ¼ atmospheric pressure (e.g., from about 2.0 psia to about 4.0 psia, in embodiments, from about 2.2 psia to about 3.8 psia) during gas transfer to the sterilizer chamber 304.

The step 402 may be performed prior to initial operation of the recycling system 302 or after the purge of thereof. The second analyzer assembly 351 also detects the concentration of ETO and other gases. The recovery tank 330 may also be refortified with the sterilant gas mixture and/or individual gases to achieve the desired sterilant gas mixture make-up based on the sensor readings.

In step 404, the objects in need of sterilization are loaded into the sterilization chamber 304 and the sterilization chamber 304 is sealed, signaling the control module 376 that the recycling system 302 is ready for operation. In step 406, a gas sample is taken of the gas mixture within the recovery tank 330. The control module 376 determines the transfer pressure, namely, the pressure needed to achieve a desired concentration setpoint for ETO based on the target and measured ETO concentrations using the formula (III) above. In addition, atmospheric conditions within the sterilizer chamber 304 and the recovery tank 330 are also measured (e.g., temperature and pressure). In embodiments, the target ETO concentration setpoint may be from about 300 mg/L to about 1000 mg/L, in embodiments, from about 400 mg/L to about 900 mg/L.

In step 408, the sterilant gas mixture from the recovery tank 330 is transferred into the sterilization chamber 304 in a substantially similar manner as described above with respect to FIGS. 1-4. The sterilant gas is transferred through the gas recovery assembly 308 until the previously calculated transfer pressure is reached. The sterilant gas mixture is transferred at a relatively constant rate that is within acceptable tolerances to prevent damage to the objects being sterilized. During the transfer, the gas circulation assembly 328 and the analyzer piping 380 are shut off from the sterilizer chamber 304 and the sterilizer chamber 304 is filled with the sterilant gas mixture.

In step 410, after the transfer of the sterilant gas mixture is completed, stabilization dwell is commenced, during which the sterilant gas mixture is stabilized for a predetermined period of time (e.g., from about 5 minutes to about 30 minutes, in embodiments, from about 10 minutes to about 20 minutes). During the stabilization dwell, the analyzer piping 380 is opened to allow for the first analyzer assembly 350 to test the temperature and the amount of ETO present in the mixture. Immediately following the gas transfer of the sterilant gas mixture to the sterilizer chamber 304, the sterilizer gas mixture has non-uniform humidity, gas concentration, and temperature. Also the sensors of the first analyzer assembly 350 instruments tend to read inaccurate values. After the stabilization dwell, the readings from the sensors of the first analyzer assembly 350 output consistent values that more accurately represent the true characteristics of the sterilant gas mixture in the sterilizer chamber 304.

Based on the sensor readings, the temperature and the ETO concentration are adjusted if needed. Temperature is adjusted by varying the water temperature of the jacket hydronic heating systems of the sterilizer chamber 304 and/or the recovery tank 330 to provide for consistent temperature within the sterilizer chamber 304. The concentration of ETO gas is checked by the analyzer assembly 350 (e.g., 4 minutes into stabilization dwell) to verify ETO concentration is within tolerances. If the concentration is too high, a partial recovery is started, sending sterilant gas mixture back to the recovery tank 330. If the concentration is too low, a partial transfer is initiated to transfer more of the sterilant gas mixture from the recovery tank 330. The analyzer assembly 350 continuously monitors the adjustment and controls the transfer of the sterilant gas mixture to or from the recovery tank 330 and terminates partial recovery or transfer once the ETO concentration is within the specified range.

In step 412, exposure dwell is commenced, during which the objects are exposed to the sterilant gas mixture for a sufficient period of time at target temperature, pressure, humidity and sterilant gas density to achieve sterilization. The gas circulation assembly 328 is opened and the circulation fans 334 are activated to commence circulation of the sterilant gas mixture through the sterilization chamber 304. Circulation aids in the sterilization process by increasing the exposure of the objects to the ETO molecules. The duration of the exposure dwell may be from about 60 minutes to about 12 hours, in embodiments, from about 90 minutes to about 10 hours, based on the density and packaging of the products being sterilized (e.g., plastic products require specific dwell times for the sterilant gas mixture to effect sterilization, etc. See e.g., ISO 11135-2007). During the exposure dwell, the control module 376 logs various properties of the sterilant gas mixture such as pressure, temperature, humidity, and ETO concentration.

In step 414, the concentration of ETO gas is checked by the analyzer assembly 350 (e.g., 35 minutes into exposure dwell) to verify ETO concentration. Based on the determined concentration, the control module 376 calculates an amount of enrichment needed to compensate for the lost ETO (e.g., absorbed by the objects during sterilization). ETO gas is added through the ETO supply 310 using a weight scale system to meter out the desired amount of gas.

In step 416, once the exposure dwell is completed, the sterilant gas mixture from the sterilization chamber 304 is transferred back into the recovery tank 330 through the gas recovery assembly 308. During the transfer, the gas circulation assembly 328 and the analyzer piping 380 are shut off from the sterilizer chamber 304 until the sterilizer chamber 304 is emptied of the sterilant gas mixture.

While the above disclosure has been focused on ETO as a sterilant gas, the system and methods of the present disclosure may be utilized with other sterilant gases within the purview of those skilled in the art. While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A system for recovery of a sterilant gas mixture from a sterilizer chamber, the system comprising:
    a gas recovery tank;
    a sterilizer chamber in gaseous communication with the gas recovery tank;
    a gas recovery assembly coupled to the gas recovery tank and the sterilizer chamber, wherein the gas recovery assembly is configured to transfer a sterilant gas mixture including at least one sterilant gas between the sterilizer chamber and the gas recovery tank;
    an analyzer assembly coupled to the sterilizer chamber, the analyzer assembly including at least one sterilant gas sensor configured to detect density of the sterilant gas; and
    a control module coupled to the analyzer assembly and to the gas recovery assembly, the control module configured to determine a transfer pressure for achieving a desired concentration of the sterilant gas and flammability of the sterilant gas mixture as a function of the density of the sterilant gas.

2. A system according to claim 1, wherein the analyzer assembly further includes:
    a pressure sensor;
    a temperature sensor; and
    at least one relative humidity sensor.

3. A system according to claim 1, wherein the at least one control module configured to determine concentration of the at least one sterilant gas.

4. A system according to claim 3, wherein the at least one control module is configured to determine at least one of the transfer pressure and flammability of the sterilant gas mixture as a function of the concentration of the at least one sterilant gas.

5. A system according to claim 1, further comprising a gas circulation assembly in gaseous communication with the sterilizer chamber, the gas circulation assembly comprising at least one circulation fan configured to circulate the sterilant gas mixture through the sterilizer chamber.

6. A system according to claim 1, wherein the gas recovery assembly further comprises first and second vacuum pumps coupled in series.

7. A method for recovery of a sterilant gas mixture from a sterilizer chamber, the method comprising:
    detecting a density of at least one sterilant gas present in a sterilant gas mixture;
    detecting concentration of the at least one sterilant gas present in the sterilant gas mixture as a function of the density thereof;
    calculating a transfer pressure for achieving a desired concentration of the sterilant gas and flammability of the sterilant gas mixture as a function of the concentration of the at least one sterilant gas; and
    transferring the sterilant gas mixture from a gas recovery tank to a sterilizer chamber via a gas recovery assembly.

8. A method according to claim 7, further comprising detecting temperature and pressure within the sterilizer chamber.

9. A method according to claim 7, further comprising:
    calculating flammability of the sterilant gas mixture as a function of the concentration of the at least one sterilant gas.

10. A method according to claim 7, further comprising:
    circulating the sterilant gas mixture through the sterilizer chamber.

11. A method according to claim 7, further comprising:
    calculating the transfer pressure of the sterilant gas mixture as a function of a target sterilant gas concentration.

12. A method for recovery of a sterilant gas mixture from a sterilizer chamber, the method comprising:

detecting adensity of at least one sterilant gas present in a sterilant gas mixture;
detecting concentration of the at least one sterilant gas present in the sterilant gas mixture as a function of the density thereof;
calculating a transfer pressure for achieving a desired concentration of the sterilant gas and flammability of the sterilant gas mixture as a function of the concentration of the at least one sterilant gas and a target sterilant gas concentration; and transferring the sterilant gas mixture from a gas recovery tank to a sterilizer chamber via a gas recovery assembly.

13. A method according to claim 12, further comprising:
detecting atmospheric conditions within the sterilizer chamber.

14. A method according to claim 12, further comprising:
circulating the sterilant gas mixture through the sterilizer chamber.

* * * * *